United States Patent
Bouguerra

(10) Patent No.: US 9,084,548 B2
(45) Date of Patent: Jul. 21, 2015

(54) VENTRICULAR FIBRILLATION DETECTION

(75) Inventor: Radouane Bouguerra, San Diego, CA (US)

(73) Assignee: Braemar Manufacturing, LLC, Eagan, MN (US)

( * ) Notice: Subject to any disclaimer, the term of this patent is extended or adjusted under 35 U.S.C. 154(b) by 337 days.

(21) Appl. No.: 13/290,952

(22) Filed: Nov. 7, 2011

(65) Prior Publication Data

US 2013/0116585 A1    May 9, 2013

(51) Int. Cl.
*A61B 5/046*      (2006.01)
*A61B 5/00*       (2006.01)

(52) U.S. Cl.
CPC ............... *A61B 5/046* (2013.01); *A61B 5/7203* (2013.01); *A61B 5/7239* (2013.01); *A61B 5/7253* (2013.01); *A61B 5/7221* (2013.01)

(58) Field of Classification Search
USPC .......... 600/508–509, 512, 515, 518; 128/920, 128/923
See application file for complete search history.

(56) References Cited

U.S. PATENT DOCUMENTS

| | | | |
|---|---|---|---|
| 5,439,004 A | 8/1995 | Duong-Van et al. | |
| 5,857,977 A | 1/1999 | Caswell et al. | |
| 7,729,753 B2 | 6/2010 | Kremliovsky et al. | |
| 7,996,075 B2 | 8/2011 | Korzinov et al. | |
| 2008/0243020 A1 | 10/2008 | Chou | |
| 2010/0099954 A1 | 4/2010 | Dickinson et al. | |
| 2010/0204599 A1 | 8/2010 | Pu et al. | |
| 2011/0160553 A1 | 6/2011 | Talbot et al. | |
| 2012/0108934 A1 | 5/2012 | Valdes et al. | |

FOREIGN PATENT DOCUMENTS

WO    WO-2007106829 A2    9/2007

OTHER PUBLICATIONS

Amann et al, A New Ventricular Fibrillation Detection Algorithm for Automated External Defibrillators, presented in conference titled Computer in Cardiology, 2005, 559-562.
International Preliminary Report dated May 22, 2014 for Application No. PCT/US2012/030397.

*Primary Examiner* — Deborah Malamud
(74) *Attorney, Agent, or Firm* — Ropes & Gray LLP

(57) ABSTRACT

Systems and techniques are disclosed for determining the onset and offset of a ventricular fibrillation event and for distinguishing ventricular fibrillation from noise. In some examples, an electrocardiogram (ECG) signal is obtained; a transform is applied to the ECG signal to obtain an analytical pair, the analytical pair including the ECG signal and the transformed ECG signal; a speed-amplitude is determined from the analytical pair; and an onset of a ventricular fibrillation event is identified based at least one of a value of a cost function of the speed-amplitude over a window and a quantity of occurrences the speed-amplitude crosses a threshold over the window.

24 Claims, 4 Drawing Sheets

VENTRICULAR FIBRILLATION DETECTION

BACKGROUND

The present application describes systems and techniques relating to automated analysis of a cardiac signal of an organism, for example, by identifying an arrhythmia event such as a ventricular fibrillation event, its duration, and distinguishing between an identified arrhythmia event and noise in a physiological signal.

Over the years, various devices, such as an electro-cardiogram (ECG) device, have been used for monitoring hearts in living beings. The heart can be monitored for various types of arrhythmia events. For example, ventricular fibrillation ("VF") is arrhythmia event that, in some instances, can be life-threatening. Ventricular fibrillation includes various symptoms including uncontrolled twitching of muscle fibers in the lower chambers of the heart. During ventricular fibrillation, the lower chambers of the heart responsible from removing blood from the heart do not function properly. In some instances, VF can be manifested in various heart disorders including a heart attack.

The electrical activity of various organs, such as the heart or brain, can be monitored, and this electrical activity can be analyzed to look for patterns that may assist in diagnosing various conditions. For example, the electrical activity of the heart can be monitored to track various aspects of the functioning of the heart. Given the volume conductivity of the body, electrodes on the body surface or beneath the skin can display potential differences related to this activity. Anomalous electrical activity can be indicative of disease states or other physiological conditions ranging from benign to fatal.

SUMMARY

Because an arrhythmia event such as ventricular fibrillation ("VF") is an abnormal rhythm in a physiological signal, it can often appear deceptively similar to random noise. This disclosure relates to systems and techniques for distinguishing between random noise and arrhythmic events, such as VF, in a physiological signal. The systems and techniques described here can be used to identify a potential VF event and determine whether the potential event is an actual event or an artifact due to noise. For example, both the onset and the offset of a VF event can be identified and the VF event can be distinguished from noise.

In a first aspect, a method for detecting a ventricular fibrillation event in an electrocardiogram (ECG) signal, can include obtaining an ECG signal; applying a transform to the ECG signal to obtain an analytical pair, the analytical pair including the ECG signal and the transformed ECG signal; determining a speed-amplitude from the analytical pair; and identifying an onset of a ventricular fibrillation event based on at least one of a value of a cost function of the speed-amplitude over a window and a quantity of occurrences that the speed-amplitude crosses a threshold over the window.

In some examples, the transformation of this method includes a Hilbert transformation. Also, the threshold can include a first threshold; and the identifying the onset of the ventricular fibrillation event can include identifying the onset of the ventricular fibrillation based on the value of the cost function of the speed-amplitude over the window, the quantity of occurrences that the speed-amplitude crosses the first threshold over the window, and a quantity of occurrences that the speed amplitude crosses a second, different threshold over the window. In some examples, identifying the onset of the ventricular fibrillation event includes determining for the window that the value of the cost function meets a first parameter, the quantity of occurrences that the speed-amplitude crosses the first threshold over the window meets a second parameter, and the quantity of occurrences that the speed amplitude crosses the second threshold meets a third parameter. Additionally, the first parameter can include a first predetermined range, the second parameter can include a second predetermined range, the third parameter can include a predetermined value, determining for the window that the value of the cost function meets the first parameter includes determining for the window that the value of the cost function is within the first predetermined range; determining that the quantity of occurrences that the speed-amplitude crosses the first threshold over the window meets the second parameter includes determining that the quantity of occurrences that the speed-amplitude crosses the first threshold is within the second predetermined range; and determining that the quantity of occurrences that the speed-amplitude crosses the second threshold meets the third parameter includes determining that the quantity of occurrences that the speed-amplitude crosses the second threshold exceeds the predetermined value. In some examples, the method can include determining for one or more other windows consecutive to the window a quantity of occurrences that a speed-amplitude determined for the one or more other windows crosses the first threshold, a value of the cost function of the speed-amplitude for the one or more other windows, and a quantity of occurrences that the speed amplitude for the one or more consecutive windows crosses the second threshold; and wherein identifying the onset of the ventricular fibrillation event can include determining for the one or more other windows that: the value of the cost function for the one or more other windows meets the first parameter, the quantity of occurrences that the speed-amplitude for the one or more other windows crosses the second threshold meets the second parameter, and the quantity of occurrences that the speed-amplitude for the one or more other windows crosses the third threshold meets the third parameter.

In some examples, the ECG signal comprises a signal for a first channel and a signal for a second channel; and the method further includes: determining for the window a maximum of a value of the cost function of the signal for the first channel and a value of the cost function of the signal for second channel, and determining a maximum value of a quantity of occurrences that the signal for the first channel crosses a predetermined ECG threshold and a quantity of occurrences that the signal for the second channel crosses the predetermined ECG threshold; and wherein identifying the onset of a ventricular fibrillation event comprises determining the onset of the ventricular fibrillation based on the maximum value of the cost functions for the first channel and the second channel and the maximum value of the quantity of occurrences that the ECG signal crosses the predetermined ECG threshold for the first channel and the second channel. In some examples, the ECG signal includes a signal for a first channel and a signal for a second channel; and determining a speed-amplitude from the analytical pair includes determining an average of a speed-amplitude for the signal of the first channel and a speed-amplitude for the signal of the second channel.

In another aspect, a method includes: obtaining an electrocardiogram (ECG) signal; applying a transform to the ECG signal to obtain an analytical pair, the analytical pair including the ECG signal and the transformed ECG signal; determining a speed-amplitude from the analytical pair; and identifying an offset of a ventricular fibrillation event based on at least one of a value of a cost function of the speed-amplitude over a window and a quantity of occurrences that the speed-amplitude crosses a threshold over the window. In some examples, the transform includes a Hilbert transform. Also, identifying the offset of the ventricular fibrillation event can include: determining the offset of the ventricular fibrillation event based on the quantity of occurrences that the speed-amplitude over a window crosses a predetermined threshold and based on a quantity of occurrences that a speed-amplitude for one or more other windows consecutive to the window crosses the predetermined threshold.

Other embodiments of these aspects include corresponding systems, apparatus, and computer programs, configured to perform the actions of the methods, encoded on computer storage devices. Details of one or more implementations are set forth in the accompanying drawings and the description below. Other features, aspects, and potential advantages will be apparent from the description and drawings, and from the claims.

DESCRIPTION OF DRAWINGS

Like reference symbols in the various drawings indicate like elements.

DETAILED DESCRIPTION

Figure 1:
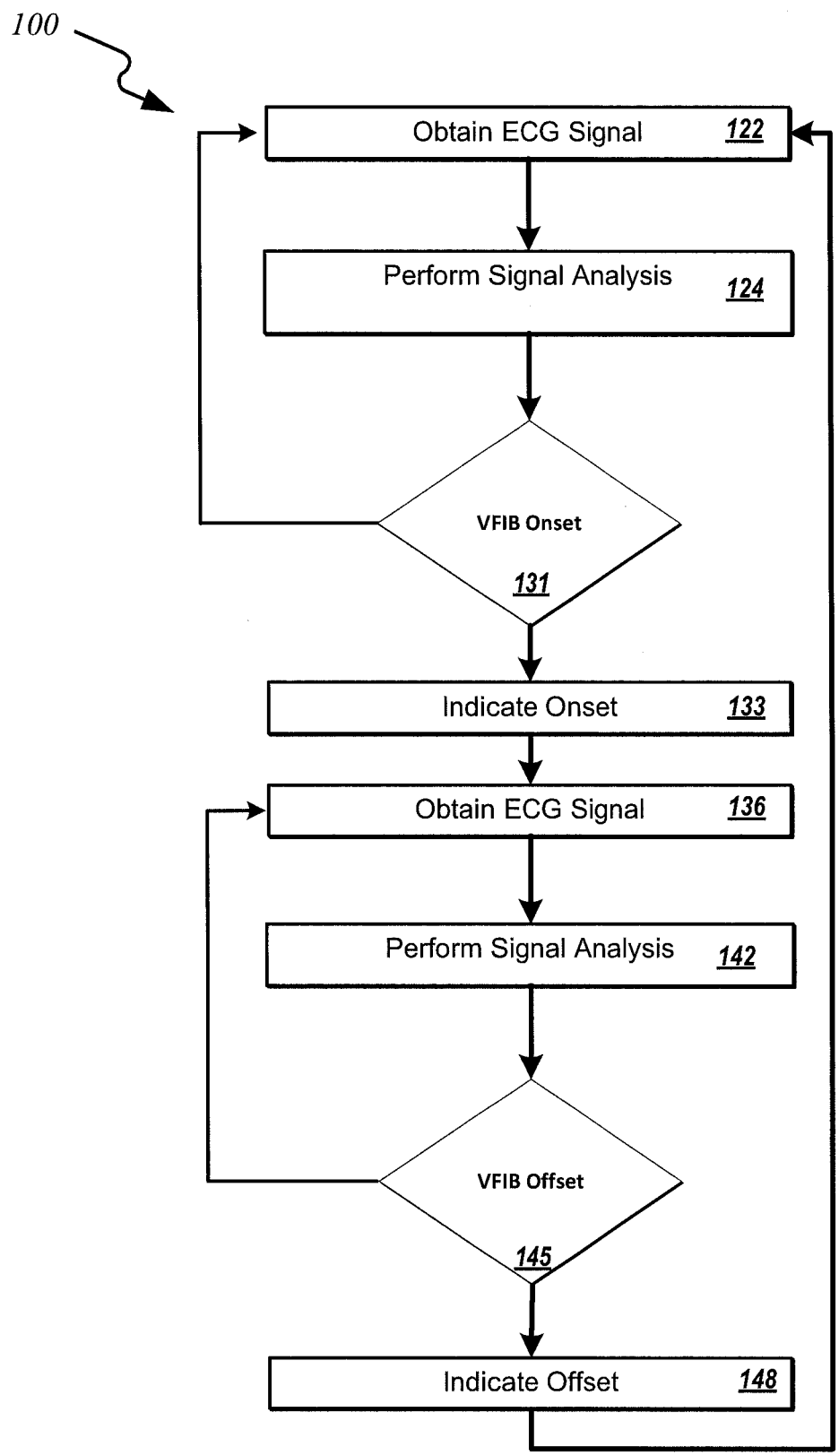
FIG. 1 shows an example process for detecting ventricular fibrillation onset and offset.

FIG. 1 shows an example process 100 for detecting ventricular fibrillation onset and for detecting ventricular fibrillation offset. At 122, an ECG signal is obtained using, for example, a cardiac monitoring system. The ECG signal can also be obtained, for example, from a data storage device. At 124, signal analysis can be performed on the ECG signal. Signal analysis can include, for example, determining an analytical pair using the obtained ECG signal. To determine an analytical pair, the ECG signal can be transformed using a transform such as a Hilbert transform. The transform and the obtained ECG signal can form a time-varying analytical pair. As discussed in more detail below, signal analysis can also include determining one or more of the following parameters for a time window: a momentum of trajectory (speed-amplitude) from the analytical pair, a cost function of the speed-amplitude, a quantity of threshold crossings for the speed-amplitude, a quantity of threshold crossings of the derivative of the speed-amplitude, a quantity of threshold crossings of the obtained ECG signal, and a cost function of the obtained ECG signal.

At 131, VF onset is identified using one or more of the above parameters determined during signal analysis. Not only can VF onset be determined using one or more of those parameters, but VF can also be distinguished from noise using such parameters. If VF onset is not detected the process 100 begins again at 122. If VF onset is detected, the process 100 indicates at 133 that there is a VF onset, such as by setting an annotation in the ECG signal with a time stamp indicating the time of onset of VF.

At 136, an ECG signal is obtained for one or more subsequent windows. At 142, signal analysis is performed on the obtained ECG signal for the one or more subsequent windows, which includes transforming the ECG signal and obtaining an analytical pair. Signal analysis also includes determining one or more of the following parameters: a speed-amplitude from the analytical pair, a cost function of the speed-amplitude, a count of a quantity of threshold crossings for the speed-amplitude, a quantity of threshold crossings of the derivative of the speed-amplitude, a quantity of threshold crossings of the obtained ECG signal, and a cost function of the obtained ECG signal. Based on one or more of those parameters, it is determined whether VF offset has occurred at 145. If offset is not detected the process 100 returns to step 136 and VF offset is checked for the next window. If offset is detected, then an indication of the VF offset is set at 148, such as by annotating the ECG signal with a time stamp, and the process 100 continues from step 122 for the next window.

Figure 2:
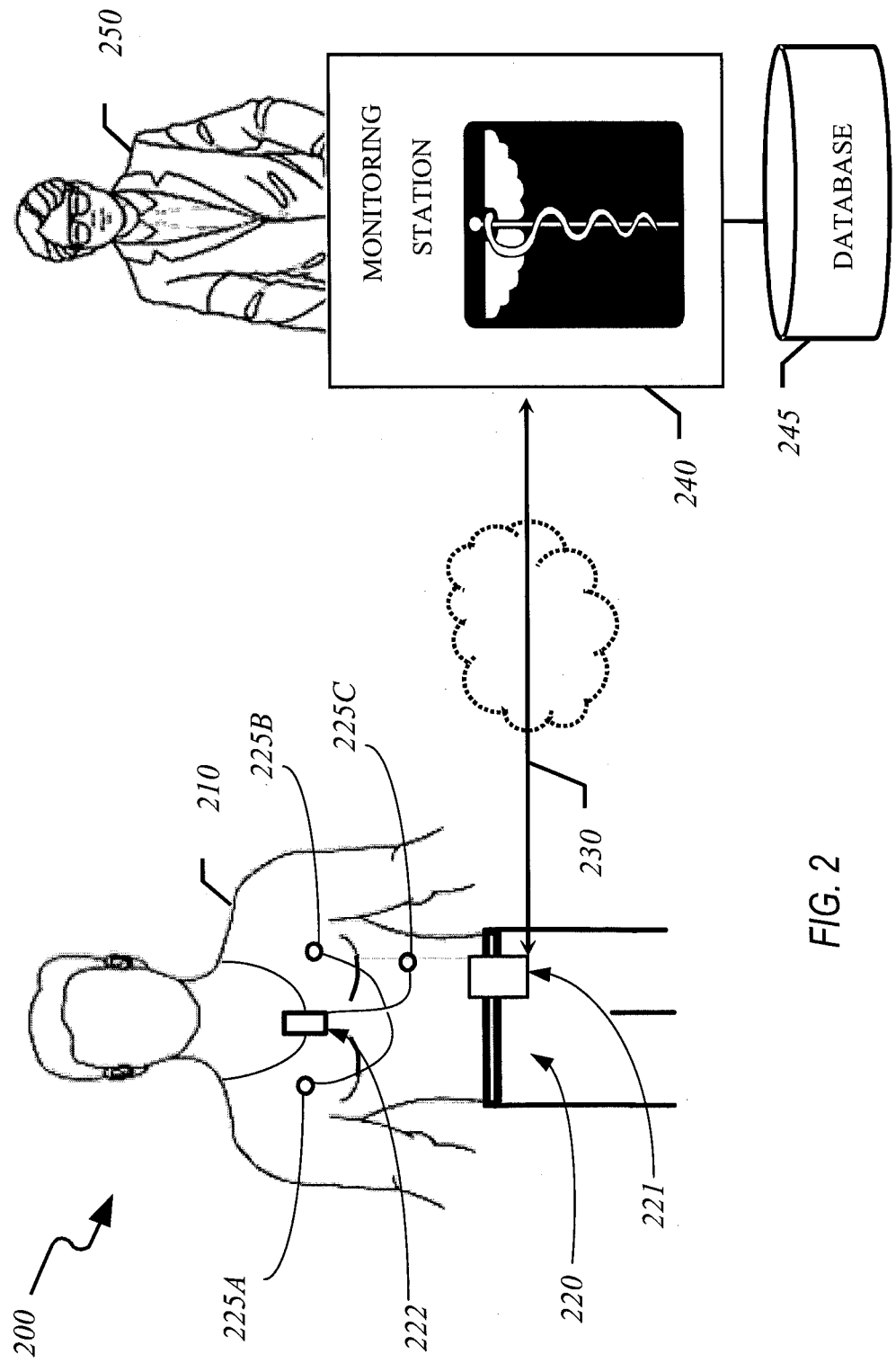
FIG. 2 illustrates an example of a distributed cardiac activity monitoring system.

The techniques described herein can be implemented on a computer system comprising one or more data processing apparatus. For example, FIG. 2 illustrates an example of a distributed cardiac activity monitoring system 200 in which a cardiac signal is monitored for medical purposes. An organism 210 (e.g., a human patient, including potentially a healthy patient for whom cardiac monitoring is nonetheless deemed appropriate) has a cardiac monitoring apparatus 220 configured to obtain cardiac signals from the patient's heart. The cardiac monitoring apparatus 220 can be composed of one or more devices, such as a processing device 221 and a sensing device 222. The sensing device can include independent leads each having a surface electrode, body surface electrodes 225A, 225B, and 225C. The independent leads can receive electrical signals through the body surface electrodes 225A, 225B, and 225C as shown (e.g., silver/silver chloride electrodes, which can be positioned at defined locations to aid in monitoring the electrical activity of the heart).

The body surface electrode 225A is positioned on the patient's chest near the patient's right arm; the body surface electrode 225B is positioned on the patient's chest near the patient's left arm; and the body surface electrode 225C is positioned just below the patient's chest near the patient's left leg. The potential difference between the right arm and the left leg forms a first channel while the potential difference between the left arm and the right arm form a second channel. An ECG signal of the patient is detected by the sensing device 222 via the first channel and the second channel. In some examples, the monitoring apparatus can use only one channel to detect an ECG signal of the patient. In some examples, the monitoring apparatus can use 3 or more channels to detect the patient's ECG signal.

The cardiac monitoring apparatus 220 can communicate with a monitoring station 240 (e.g., a computer in a monitoring center) via a communications channel 230. The cardiac monitoring apparatus 220 can include one or more sensing, calibration, signal processing, control, data storage, and transmission elements suitable for generating and processing the cardiac signal, as well as for relaying all or a portion of the cardiac signal over the communications channel 230. The communications channel 230 can be part of a communications network and can include any suitable medium for data transmission, including wired and wireless media suitable for carrying optical and/or electrical signals. Wireless communications by the apparatus 220 can employ a suitable antenna.

The cardiac monitoring apparatus 220 can communicate sensed cardiac signals, cardiac event information (e.g., real-time heart rate data), and additional physiological and/or other information to the monitoring station 240. In some examples, the cardiac monitoring apparatus 220 can include an implantable medical device, such as an implantable cardiac defibrillator and an associated transceiver or pacemaker and an associated transceiver, or an external monitoring device that the patient wears or that is installed near the patient. Moreover, the cardiac monitoring apparatus 220 can be implemented using, for example, the CardioNet Mobile Cardiac Outpatient Telemetry (MCOT) device, which is commercially available and provided by CardioNet, Inc. of Conshohocken, Pa.

The monitoring station 240 can include a receiver element for receiving transmitted signals, as well as various data processing and storage elements for extracting and storing information carried by transmissions regarding the state of the organism 210. The monitoring station 240 can be located in the same general location (e.g., in the same room, building or health care facility) as the monitoring apparatus 220, or at a remote location. The monitoring station 240 can include a display and a processing system, and a system operator 250 (e.g., a doctor or a cardiovascular technician) can use the monitoring station 240 to evaluate physiological data received from the cardiac monitoring apparatus 220. The system operator 250 can use the monitoring station 240 to change operational settings of the cardiac monitoring apparatus 220 remotely during active cardiac monitoring of the organism 210.

Moreover, the cardiac monitoring apparatus 220 and/or the monitoring station 240 can use the systems and techniques described herein to identify physiological information concerning the organism 210. This can include signal processing and analysis on both an actively received signal and prior signals stored in a database 245. For example, historical signal information for a person can be used in conjunction with the systems and techniques described herein to improve analysis of currently acquired signals, and can facilitate heart beat classification and characterization of physiological conditions, which can assist a clinician or physician in making an appropriate diagnosis and prescribing an appropriate treatment.

Figure 3:
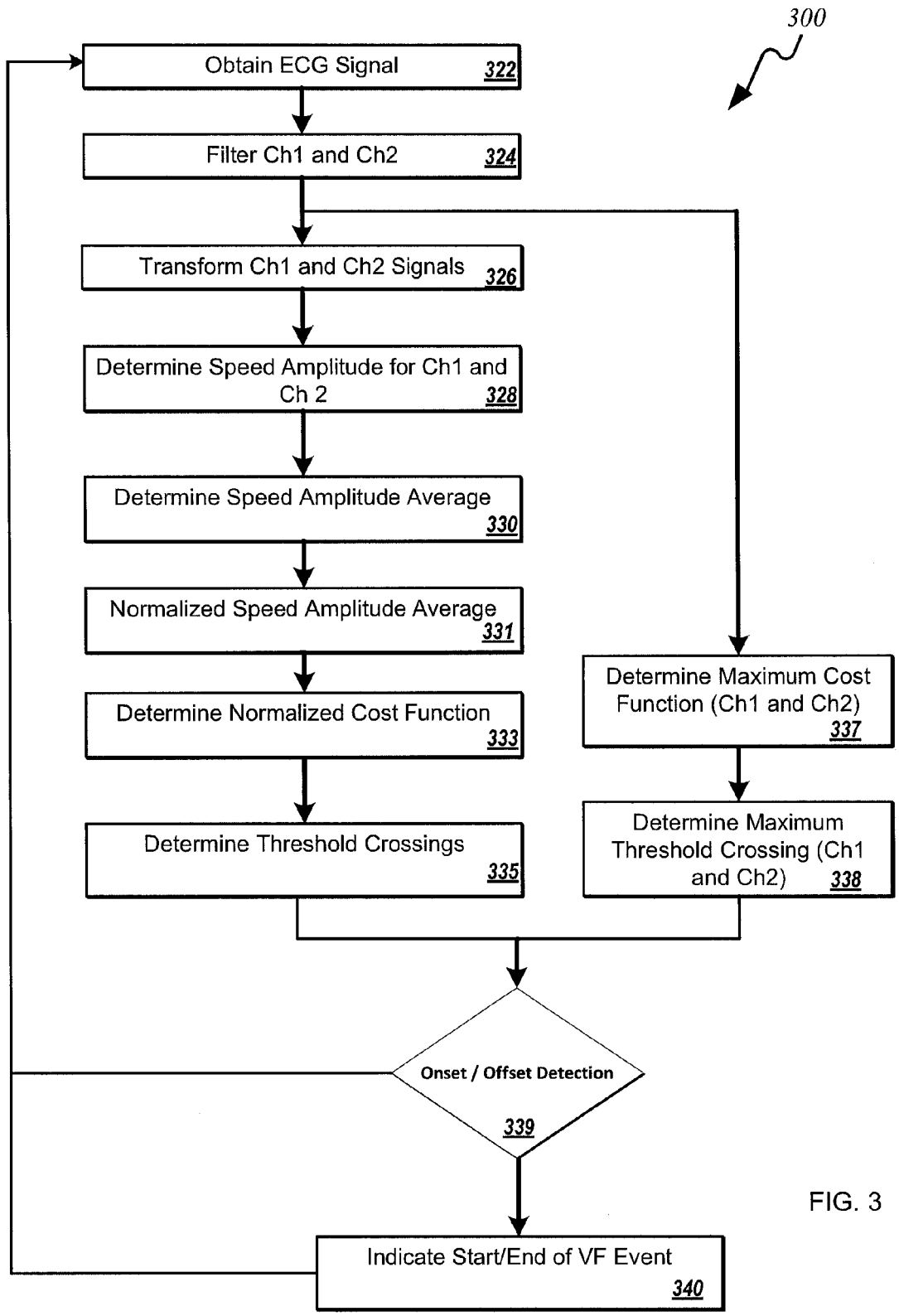
FIG. 3 shows an example process for detecting onset and offset of ventricular fibrillation.

FIG. 3 shows an example process 300 for detecting onset and offset of ventricular fibrillation. Process 300 can be used to distinguish ventricular fibrillation from noise. At 322, a raw ECG signal is obtained. The ECG signal can be obtained from an ambulatory patient using a monitoring system such as cardiac activity monitoring system 200 described above. The ECG signal can be analyzed real-time as it is obtained by such a monitoring system. In some examples, the ECG signal is obtained from a database or from a storage device, storing ECG data from a patient.

The ECG signal can include multiple channels. For example, process 300 is described in the context of a two channel system with a first channel ("ch1") and a second channel ("ch2"). The ECG signal can be obtained at various sampling rates, such as at a sampling rate between 125 Hz and 500 Hz. At a sampling rate of 250 Hz, in one second there will be 250 samples for channel 1 and 250 samples for channel 2. Process 300 can also be performed for a single channel ECG signal by, for example, setting one of the channels to zero and skipping the step 330. Process 300 can also be performed using three or more channels. For example, the most dominant channel or the most dominant two channels can be selected for use in this process. Also, principal component analysis can be performed to reduce the dimension of channels from three or more channels to one channel or to two channels.

At 324, the obtained ECG signal is filtered. Various types of filtering can be performed on the signal to prepare the signal for further analysis. For example, the raw ECG signal can be passed through a bandpass filter that limits the bandwidth of the signal to isolate a portion of the signal for ECG analysis. Also, filtering can be performed to remove baseline wandering in the ECG signal.

At 326, the obtained ECG signal is transformed using a transform. For example, the obtained ECG signal can be transformed using a Hilbert Transformation. The process 300 is described in the context of a Hilbert Transformation, but other transformations can be used. For example, other orthogonal transforms can be used. Obtaining a transformation of the ECG can include obtaining a derivative of the ECG signal. For a two channel system, the Hilbert transform is performed on both channels. For example, a Hilbert Transformation, H(t), of an input ECG signal, x(t), produces a complex signal $j\hat{x}(t)$. The Hilbert transform and the ECG signal form an analytical pair, $\vec{A}(t)$, which equals $x(t)+j\hat{x}(t)$. The analytical pair, x(t) and H(x(t)) together, forms a partial state space trajectory.

At 326, speed-amplitude is determined. For example, a momentum of trajectory can be derived from the amplitude property of the partial state space trajectory and the amplitude of the speed of trajectory. In a two channel system, the speed-amplitude, spAmp, is determined for both channels. The speed-amplitude is the product of the speed and amplitude as determined from the analytical pair, $\vec{A}(t_i)$, such that:

$$spAmp = speed * amplitude.$$

For a current sample, i, of the ECG signal the analytical pair can be represented as $\vec{A}(t_i)=x(t_i)+j\hat{x}(t_i)$. The analytical pair for k samples away (k can be, e.g., 1 (for an adjacent sample), 2, 3, 4, 8, 10 etc.) from the current sample can be represented by $\vec{A}(t_{i+k})=x(t_{i+k})+j\hat{x}(t_{i+k})$. $\Delta\vec{A}(t_{i+k})$ is the change in the two vectors $(x(t_i), \hat{x}(t_i))$ and $(x(t_{i+k}), \hat{x}(t_{i+k}))$. In other words, $$\Delta\vec{A}(t_{i+k}) = \vec{A}(t_{i+k}) - \vec{A}(t_i) = [x(t_{i+k}) - x(t_i)] + j[\hat{x}(t_{i+k}) - \hat{x}(t_i)]$$

Speed is the derivative of the analytical pair. Speed for i+k can be calculated as follows:

$$speed = |\Delta\vec{A}(t_{i+k})| = \sqrt{(x(t_{i+k}) - x(t_i))^2 + (\hat{x}(t_{i+k}) - \hat{x}(t_i))^2}$$

Amplitude for i+k can be calculated as follows:

$$amplitude = |\vec{A}(t_{i+k})| = \sqrt{(x(t_{i+k}) - x(t_i))^2 + (\hat{x}(t_{i+k}) - \hat{x}(t_i))^2}$$

Speed-amplitude is the product of speed and amplitude such that $$spAmp(t_{i+k}) = |\vec{A}(t_{i+k})| * |\Delta\vec{A}(t_{i+k})|$$

At 330, the speed-amplitude for a given sample of channel 1 and channel 2 is averaged as follows for time i+k:

$$\overline{spAmp(t_{i+k})} = \frac{smAmpCh1(t_{i+k}) + spAmpCh2(t_{i+k})}{2}.$$

This is performed sample by sample such that an averaged time varying single, $\overline{spAmp(t)}$ is obtained.

In a single channel example, this step can be omitted. In such an example, $\overline{spAmp(t)}$ is the time varying signal obtained by calculating $spAmp(t_{i+k})$ for a series of samples for the single channel. Using multiple channels helps decrease the risk of missing a ventricular fibrillation event due to excessive noise in one of the channels. In some examples, signal quality for each channel of multiple channels can be analyzed. The process 300 can proceed with the speed-amplitude of the cleanest channel.

At 331, a window, $W_1$, of samples of the time varying average of speed-amplitude signal, $\overline{spAmp(t)}$, is normalized, becoming a multiple sample normalized vector, $\overline{spAmpAve(t)}$. For example, the window, $W_1$, can include all of the averaged samples in one second. For a 250 Hz sampling rate, the one second window, $W_1$, includes 250 samples. To normalize the speed-amplitude average for the window, $W_1$, for example, each sample is centered by subtracting the mean of all the samples in the window from each sample in the window and then dividing each sample by the maximum sample in the window so that the samples in the window, $W_1$, are centered between zero and one.

The following pseudo-code provides an example of how the normalized $\overline{spAmpAve(t)}$ vector can be calculated:

spAmp_normalized=(spAmp_Average−mean(spAmp_Average))/max(spAmp_Average);

where spAmp_Average is a vector of the average of the spAmp of two channels for the window, $W_1$, averaged sample by sample (e.g., 250 samples); mean(spAmp_Average) is the mean spAmp of all of the samples in the window, $W_1$; and the max(spAmp_Average) is the maximum value of the spAmp_Average vector.

At 333, a cost function, such as an additive information cost function, is applied to the normalized speed-amplitude average vector $\overline{spAmpAve(t)}$ to determine the energy of the signal. The cost function can be calculated in various ways. For example, the cost function can be calculated by taking the sum of the absolute values of each point in the normalized $\overline{spAmpAve(t)}$ vector, which can be referred to as calculating in L1 space. In some examples, the cost function can be calculated by taking the sum of the square of each point in the vector, which can be referred to as calculating in L2 space. Other cost functions can be used such as an entropy cost function. The cost function provides an indication of the distribution of the energy in the signal. If the signal is noisy then value of the cost function will be larger. But, for less noisy signals, the value of the cost function will be lower. In other words, the cost function can help distinguish between noisy signal and a signal exhibiting ventricular fibrillation.

The cost function applied to the $\overline{spAmpAve(t)}$ vector having 250 samples can be computed, for example, as follows:

$$\text{cost} = \sum_{i=1}^{250} |\text{spAmp\_normalized}(i)|$$

At 335, threshold crossings are calculated. The quantity of occurrences that the $\overline{spAmp(t)}$ (or the normalized vector $\overline{spAmpAve(t)}$) for the window, $W_1$, and/or the quantity of occurrences that the derivative of the $\overline{spAmp(t)}$ crosses a threshold or thresholds during the window, $W_1$, can also be used to distinguish noise from actual ventricular events. For example, the cost function of ventricular fibrillation can be similar to the cost function of noisy signal. Threshold crossings can be used to help distinguish between ventricular fibrillation and noise. The following three threshold crossings can be calculated. First, the quantity of occurrences that the vector, $\overline{spAmpAve(t)}$, crosses zero (e.g., when the $\overline{spAmpAve(t)}$ is centered about zero) or the quantity of occurrences that the $\overline{spAmpAve(t)}$ crosses a first threshold such as the mean of the samples of the $\overline{spAmpAve(t)}$ can be calculated; second, the quantity of occurrences that the vector, $\overline{spAmpAve(t)}$ crosses a second threshold, such as a predetermined, empirically derived value, can be calculated; and third, the quantity of occurrences that the derivative of the vector $\overline{spAmpAve(t)}$ crosses a predetermined threshold can be calculated. One or more of these can be used to distinguish between noise and actual ventricular fibrillation events.

The three different thresholds that can be used in the process 300 can be determined, for example, as follows:

(1) Speed-Amplitude Turning Points $$nbxing1 = \sum_{i=1}^{250} |M(\text{smAmp\_Average}(i)) - M(\text{spAmp\_Average}(i-1))|$$

where:

$$M(\text{spAmp\_Average}(i)) = \begin{cases} 1, & \text{smAmp\_Average}(i) \geq MspAmp \\ 0, & \text{spAmp\_Average}(i) < MspAmp \end{cases}$$

and $M(\text{spAmp\_Average}(0)) = M(\text{spAmp\_Aveage}(1))$ where spAmp_Average is the vector, $\overline{spAmpAve(t)}$, where MspAmp is the mean value of spAmp_Average, and nbxing1 is the number of zero crossings of the spAmp_Average.

(2) Speed-Amplitude Threshold Crossing $$nbxing2 = \sum_{i=1}^{250} \text{spAmp\_Average}(i) > thLevel$$

where thLevel can be, for example set to 5, which is chosen empirically based on the momentum of trajectory (speed-amplitude product) of noisy signals compared to speed-amplitude of VFIB.

(3) Speed-Amplitude First Derivative Threshold Crossing $$nbxing3 = \sum_{i=1}^{250} DspAmp(i) < thLevel$$

where DspAmp is the derivative of spAmp_Average, and nbxing3 is the quantity of threshold crossings of the derivative of the speed-amplitude.

In some examples, the cost function and threshold crossings of the ECG signal itself can optionally be used for further accuracy in identifying ventricular fibrillation. For example, for the window, $W_1$, the cost function of the filtered ECG signal from channel 1 and from channel 2 can be determined; the maximum value of the cost function from these two channels is determined at 337. The cost function can be performed on a normalized version of the ECG signal for each channel over the window, $W_1$. At 338, the maximum value of the threshold crossings of the filtered ECG signal (e.g., the normalized ECG signal) is calculated for each of the first channel and the second channel. This information is used by process 300 to eliminate false detections of ventricular fibrillation. As shown in more detail at 339, this information determined at 337 and 338 is used to determine a signal to noise ratio; a high enough signal to noise ration can be used to cancel identified ventricular fibrillation.

The cost function of an ECG normalized signal (i.e., ecg_normalized=(ecg_data−mean(ecg_data))/max(ecg_data)) can be determined, for example, as follows:

$$ecost = \sum_{i=1}^{250} |ecg\_normalized(i)|$$

ecost is computed for both channels 1 and 2

$$ecost = \max(ecost(ch1), cost(ch2))$$

where ecost is the maximum value of the cost function of channel 1 and channel 2. The ECG Turning Points can be calculated, for example, as follows:

$$enbxing = \sum_{i=1}^{250} |M(ecg\_data(i)) - M(ecg\_data(i-1))|$$

where:

$$M(ecg\_data(i)) = \begin{cases} 1, & ecg\_data(i) \geq Mecg \\ 0, & ecg\_data(i) < Mecg \end{cases}$$

and $M(ecg\_data(0)) = M(ecg\_data(1))$ enbxing is computed for both channels 1 and 2
enbxing_max=max (enbxing(ch1), enbxing(ch2))
where enbxing is the quantity of occurrences that the ECG signal crosses a threshold for the window; where Mecg is the mean value of ecg_data vector, and where enbxing_max is the maximum of the quantity of crossings for both channels.

At 339, at least some of the cost function values determined at 333 and 337, and the threshold crossing values determined at 335 and 338 are used to determine the onset of ventricular fibrillation and to distinguish it from noise. For example, the cost function values and the threshold crossing values can be determined for a series of three windows. In the following example, each window is a one second window containing 250 samples. As described above, for each window the following variables have been calculated:

nbxing1: a quantity of occurrences that the $\overline{spAmpAve(t)}$ (spAmp) crosses a first threshold (threshold 1) over a window;

nbxing2: a quantity of occurrences that $\overline{spAmpAve(t)}$ (spAmp) crosses a second threshold (threshold 2) of over a window;

dnbxing: a quantity of occurrences that $\overline{spAmpAve(t)}$ (spAmp) crosses a third threshold over a window;

cost: a value of the cost function (energy) of $\overline{spAmpAve(t)}$ (spAmp) over a window;

ecost: a value of the cost function (energy) of the ECG signal over a window;

enbxing: a quantity of occurrences that the ECG signal crosses a fourth threshold over a window; and enbxing_max: the maximum of enbxing for the multiple channels.

If these variable meet the following conditions for each of the three consecutive windows (i-2, i-1, and i) then the onset of a VF event is identified at 340:

For the first window (i-2),
[(cost(i-2)>=25) AND (nbxing3 (i-2)<=90) AND (nbxing1(i-2)>=9) AND (nbxing1(i-2)<=22) AND (nbxing2(i-2)>=150) AND (enbxing(i-2)<=15) AND (ecost(i-2)>=100) AND (ecost(i-2)<=210)]
OR
[(nbxing3(i-2)>=3) AND (nbxing3(i-2)<=10) AND (nbxing2(i-2)>=230) AND (nbxing1(i-2)>=10) AND (nbxing1(i-2)<=22) AND(enbxing_max(i-2)<=5)].

For the second window (i-1),
[(nbxing1(i-1)>=11) AND (nbxing1(i-1)<=24) AND (nbxing2(i-1)>150) AND (enbxing(i-1)<=10) AND (ecost(i-1)>=80) AND (ecost(i-1)<=200)]
OR
[(nbxing1(i-1)>=9) AND (nbxing1(i-1)<=10) AND (nbxing2(i-1)>=210)) AND (nbxing3(i-1)<=60) AND (cost(i-1)>=35) AND (enbxing(i-1)<=13) AND (ecost(i-1)>=80) AND (ecost (i-1)<=200)].

For the third window (i),
[(nbxing1(i)>=9) AND (nbxing1(i)<=12) AND (nbxing1(i)>=150) AND (cost(i)>=40) AND (enbxing(i)<=13) AND (ecost(i)>=70) AND (ecost(i)<=200)]
OR
[(nbxing1(i)>8) AND (nbxing1(i)<=24) AND (nbxing2(i)>=210) AND (nbxing3(i)<=70) AND (cost(i)>=30) AND (enbxing(i)<=13) && (ecost(i)>=70) AND (ecost(i)<=200)].

In a 250 hz, two channel ECG signal as described above, the momentum of trajectory (speed-amplitude product) tends to oscillate between 8 and 24 threshold crossings around the mean value across window, for example a 1 second, 250 hz window such as window W1, during ventricular fibrillation episodes as compared to a noisy signal where the speed-amplitude tends to oscillate randomly with higher frequency around the mean value. During ventricular fibrillation episodes, the momentum of trajectory (speed-amplitude product) threshold crossing rate is 60% or greater of the total number of samples in a one-second window (e.g., window W1). The zero crossing rate, enbxing, and the cost function, ecost, are used to estimate the ECG channel quality, (i.e., to distinguish between a clean and a noisy ECG signal). If the zero crossing rate, enbxing, does not exceed 5% of the total number of samples in the window and the L1 cost function of the ECG signal is between 70 and 200 (for e.g., window W1), the ECG signal can be considered to be clean. Otherwise, the ECG channel is considered to be noisy and will be excluded from ventricular fibrillation episode detection.

If these criteria are met for all three consecutive windows then the onset of a VF event is identified. This identification can be made as an annotation flag in the ECG data representative of the ECG signal. The following is pseudo-code that depicts an example of this logic:

```
VFIB_Onset = false
vf_count = 4;
If(! VFIB_Onset) //VF ONSET
Previous window (i-2)
VFResult_.on = ( ( ( cost(i-2) >= 25 ) && (nbxing3 (i-2) <= 90) && (
nbxing1(i-2) >=9) && ( nbxing1(i-2) <= 22 ) && (nbxing2(i-2) >= 150)
&& ( enbxing(i-2) <= 15 ) && ( ecost(i-2) >= 100 ) && (ecost(i-2) <=
210 ) || ( (nbxing3(i-2) >= 3) && (nbxing3(i-2) <= 10) && (nbxing2(i-2)
>= 230 ) && ( nbxing1(i-2) >= 10 ) && ( nbxing1(i-2) <= 22 ) &&
(enbxing _max (i-2) <= 5 ) )
Current window (i-1)
&& ( ( (nbxing1(i-1) >= 11) && (nbxing1(i-1) <= 24 ) && (nbxing2(i-
1)_ > 150) && ( enbxing(i-1) <= 10 ) && ( ecost(i-1) >= 80 ) &&
(ecost(i-1) <= 200 ) || ( (nbxing1(i-1) >= 9 ) && (nbxing1(i-1) <= 10 )
&& (nbxing2(i-1) >= 210) ) && ( nbxing3(i-1) <= 60 ) && (cost(i-1) >=
35) && ( enbxing(i-1) <= 13 ) && ( ecost(i-1) >= 80) && (ecost(i-1) <=
200) ) );
Most Recent Window (i)
&& ( ( (nbxing1(i) >= 9 ) && (nbxing1(i) <= 12) && (nbxing2(i) >=
150) && (cost(i) >= 40 ) && ( enbxing(i)_ <= 13 ) && ( ecost(i) >=
70 ) && (ecost(i) <= 200 )) || ( (nbxing1 (i)_ > 8 ) && (nbxing1(i) <=
24 ) && (nbxing2(i) >= 210 ) && (nbxing3(i) <= 70 ) && (cost(i) >= 30
```

```
&& ( enbxing(i) <= 13 ) && ( ecost(i) >= 70 ) && (ecost(i) <= 200 ) ) )
If(VFResult_.on)
    VFIB_Onset = true
End
```

If onset is detected at 339 then at 340 the ECG signal is annotated to identify that a VF event has begun. The process 300 repeats for subsequent window(s) to test the ECG signal for VF offset. At 340, instead of testing for onset, an offset logic is used to test for VF offset, which is discussed in more detail below. If, however, onset is not detected, (e.g., in the example above, if all of the criteria for the three windows (a current window and its preceding two windows) are not met), the process 300 is repeated for the next window to test again for onset of VF.

In some examples, VF onset can be identified at 339 when: cost is within a predetermined range, nbxing1 is within a predetermined range, and nbxing2 exceeds a predetermined threshold. For example, these criteria can be: ((cost>=20 AND cost<=60) AND (nbxing1>=9 AND nbxing1<=22) AND (nbxing2>=140)) for a one second window with 250 samples. The identified VF onset can further be tested for a false detection due to noise. If the following criteria are met, then the VF onset is distinguished from noise: ecost is within a predetermined range and enbxing is below a predetermined threshold. For example, for a 1 second window with 250 samples, if the following criteria are met, then the VF onset can be distinguished from noise: ((ecost>=80 AND ecost<=200) AND (enbxing<=13)). When the above criteria for VF onset and for distinguishing from noise are met for three consecutive windows (e.g., a current window and its preceding two windows), VF onset is found and at 340, an indication, such as an annotation, is set for the ECG signal to identify the onset (e.g., the time of onset).

An example of pseudo-code for the above criteria to determine a VF onset is:

```
VFResult_.on = ( ( cost >=20 && cost <=60) && (nbxing1 >=9
&& nbxing1 <= 22) && (nbxing2 >=140) );
    noise_free = ( (ecost >=80 && ecost <= 200) && (enbxing <= 13));
    VFResult.on = VFResult_.on_ * noise_free
    if(VFResult_.on == 1) for 3 consecutive windows, then
VFIB_Onset = true(Start VF event).
```

If the criteria for a VF onset and for distinguishing from noise are not met then process 300 is repeated for the next window (using the next window's preceding two windows). If ventricular fibrillation onset is found, the ECG signal is continuously monitored to determine VF offset. For example, offset can be determined by repeating process 300 using an offset logic at 339 to determine the offset of the VF event.

For example, when the following criteria are met for a predetermined number of consecutive windows, such as four consecutive windows, an offset indication is made at 340: [(nbxing1(i)<=4) AND ((nbxing2(i)<=180) OR (ecost(i) <=90) OR (nbxing1(i)>=12))]. The following pseudo-code is an example of this criteria:

```
elseif ( ( nbxing1(i) <= 4 ) && ( (nbxing2(i) <= 180 ) || ( ecost(i) <=
90 ) || ( nbxing1(i) >= 12 ) ) )
    vf_count = vf_count - 1;
    if(vf_count == 0)
        VFIB_onset = false // VFIB Offset
    end
```
```
else
    vf_count = 4;
end
```

In the above example, the number of consecutive windows that must meet this criteria is four; detection of VFIB offset is supplied with inertia to avoid early termination of VFIB episodes. In other examples, the number could be set to any integer such as a higher number, e.g., eight consecutive windows.

Figure 4:
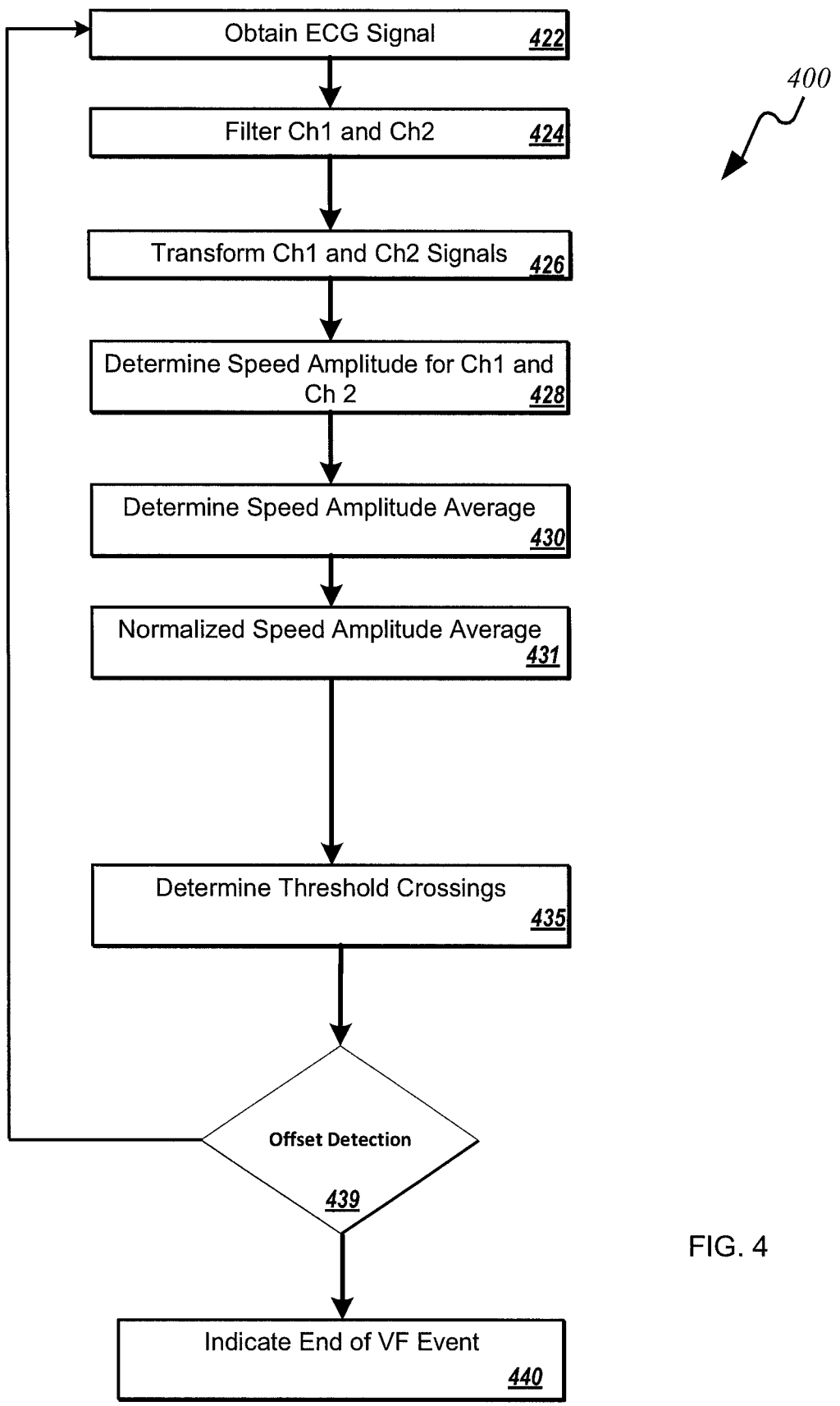
FIG. 4 shows an example process for determining for ventricular fibrillation offset.

FIG. 4 shows an example process 400 for determining for VF offset. Steps 422-435 are similar to steps 322-335. For example, at 435, threshold crossings are calculated. For example, the quantity of occurrences that the $\overline{\overline{spAmp(t)}}$ (or the normalized vector spAmpAve(t)) for the window, $W_1$, crosses a threshold or thresholds during the window, $W_1$ can be calculated. The quantity of occurrences that the $\overline{\overline{spAmpAve(t)}}$ crosses a first threshold such as the mean of the samples of the $\overline{\overline{spAmpAve(t)}}$ can be calculated; this value can be depicted by nbxing1. Second, the quantity of occurrences that the vector, $\overline{\overline{spAmpAve(t)}}$, crosses a second threshold, such as a predetermined, empirically derived value, can be calculated; this value can be depicted by nbxing2. At 439, the threshold crossing values determined at 435 are used to determine the offset of ventricular fibrillation. For example, if nbxing1 and nbxing2 are below a predetermined value for a predetermined number of consecutive windows, it is determined the VF offset has occurred. The following pseudo-code, is an example of determining VF offset:

```
VFResult_.off = ((nbxing1 <=4 && nbxing2 <= 180));
    if(VFResult_.off == 1) for the last 3 windows, then VFIB_Onset =
    false
(End VF at current position).
```

At 440, an end of a VF event is indicated. For example, the ECG signal can be annotated with a time stamp, indicating that the VF event has finished. If offset detection at 439, does not identify an end of a VF event, then the process 400 is repeated for the next consecutive window.

Details of one or more implementations are set forth in the accompanying drawings and the description below. Other features, aspects, and potential advantages will be apparent from the description and drawings, and from the claims.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices such as on or associated with a server or other computing device).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array), an ASIC (application-specific integrated circuit) or System On a Chip (SOC). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing, and grid computing infrastructures.

A computer program (also known as a program, software, software application, app, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA or an ASIC.

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending webpages to a web browser on a user's client device in response to requests received from the web browser.

Implementations of the subject matter described in this specification can be implemented in a computing system that includes a back-end component, e.g., as a data server, or that includes a middleware component, e.g., an application server, or that includes a front-end component, e.g., a client computer having a graphical user-interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network ("LAN") and a wide area network ("WAN"), an inter-network (e.g., the Internet), and peer-to-peer networks (e.g., ad hoc peer-to-peer networks).

The computing system can include clients and servers. A client and server are generally remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

While this specification contains many specific implementation details, these should not be construed as limitations on the scope of any implementations or of what may be claimed, but rather as descriptions of features specific to particular implementations of particular implementations. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

Thus, particular implementations of the subject matter have been described. Other implementations are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

What is claimed is:

1. A method for detecting a ventricular fibrillation event in an electrocardiogram (ECG) signal, the method comprising:
    obtaining an ECG signal;
    applying a transform to the ECG signal to obtain an analytical pair, the analytical pair including the ECG signal and the transformed ECG signal;
    determining a speed-amplitude from the analytical pair; and
    identifying an onset of a ventricular fibrillation event based on a value of a cost function of the speed-amplitude over a window.

2. The method of claim 1, wherein the transformation comprises a Hilbert transformation.

3. The method of claim 1,
    wherein the identifying an onset of a ventricular fibrillation event is based on a quantity of occurrences that the speed-amplitude crosses a threshold over the window;
    wherein the threshold comprises a first threshold; and
    wherein identifying the onset of the ventricular fibrillation event comprises identifying the onset of the ventricular fibrillation based on:
        the value of the cost function of the speed-amplitude over the window,
        the quantity of occurrences that the speed-amplitude crosses the first threshold over the window, and
        a quantity of occurrences that the speed amplitude crosses a second, different threshold over the window.

4. The method of claim 3, wherein identifying the onset of the ventricular fibrillation event comprises determining for the window that:
    the value of the cost function meets a first parameter,
    the quantity of occurrences that the speed-amplitude crosses the first threshold over the window meets a second parameter, and
    the quantity of occurrences that the speed amplitude crosses the second threshold meets a third parameter.

5. The method of claim 4,
    wherein the first parameter comprises a first predetermined range,
    wherein the second parameter comprises a second predetermined range,
    wherein the third parameter comprises a predetermined value,
    wherein determining for the window that the value of the cost function meets the first parameter comprises determining for the window that the value of the cost function is within the first predetermined range;
    wherein determining that the quantity of occurrences that the speed-amplitude crosses the first threshold over the window meets the second parameter comprises determining that the quantity of occurrences that the speed-amplitude crosses the first threshold is within the second predetermined range; and
    wherein determining that the quantity of occurrences that the speed-amplitude crosses the second threshold meets the third parameter comprises determining that the quantity of occurrences that the speed-amplitude crosses the second threshold exceeds the predetermined value.

6. The method of claim 4, further comprising:
    determining for one or more other windows consecutive to the window:
        a quantity of occurrences that a speed-amplitude determined for the one or more other windows crosses the first threshold,
        a value of the cost function of the speed-amplitude for the one or more other windows, and
        a quantity of occurrences that the speed amplitude for the one or more consecutive windows crosses the second threshold; and
    wherein identifying the onset of the ventricular fibrillation event comprises determining for the one or more other windows that:
        the value of the cost function for the one or more other windows meets the first parameter,
        the quantity of occurrences that the speed-amplitude for the one or more other windows crosses the second threshold meets the second parameter, and
        the quantity of occurrences that the speed-amplitude for the one or more other windows crosses the third threshold meets the third parameter.

7. The method of claim 1,
    wherein the identifying an onset of a ventricular fibrillation event is based on a quantity of occurrences that the speed-amplitude crosses a threshold over the window;
    wherein the ECG signal comprises a signal for a first channel and a signal for a second channel;
    and further comprising:
        determining for the window a maximum of a value of the cost function of the signal for the first channel and a value of the cost function of the signal for second channel, and
        determining a maximum value of a quantity of occurrences that the signal for the first channel crosses a predetermined ECG threshold and a quantity of occurrences that the signal for the second channel crosses the predetermined ECG threshold; and
    wherein identifying the onset of a ventricular fibrillation event comprises determining the onset of the ventricular fibrillation based on the maximum value of the cost functions for the first channel and the second channel and the maximum value of the quantity of occurrences that the ECG signal crosses the predetermined ECG threshold for the first channel and the second channel.

8. The method of claim 1,
wherein the ECG signal comprises a signal for a first channel and a signal for a second channel; and
wherein determining a speed-amplitude from the analytical pair comprises determining an average of a speed-amplitude for the signal of the first channel and a speed-amplitude for the signal of the second channel.

9. A non-transitory machine-readable medium encoding a computer program product operable to cause data processing apparatus to perform operations comprising:
obtaining an ECG signal;
applying a transform to the ECG signal to obtain an analytical pair, the analytical pair including the ECG signal and the transformed ECG signal;
determining a speed-amplitude from the analytical pair; and
identifying an onset of a ventricular fibrillation event based on a value of a cost function of the speed-amplitude over a window.

10. The machine-readable medium of claim 9, wherein the transformation comprises a Hilbert transformation.

11. The machine-readable medium of claim 9,
wherein the identifying an onset of a ventricular fibrillation event is based on a quantity of occurrences that the speed-amplitude crosses a threshold over the window;
wherein the threshold comprises a first threshold; and
wherein identifying the onset of the ventricular fibrillation event comprises identifying the onset of the ventricular fibrillation based on:
the value of the cost function of the speed-amplitude over the window,
the quantity of occurrences that the speed-amplitude crosses the first threshold over the window, and
a quantity of occurrences that the speed amplitude crosses a second, different threshold over the window.

12. The machine-readable medium of claim 11, wherein identifying the onset of the ventricular fibrillation event comprises determining for the window that:
the value of the cost function meets a first parameter,
the quantity of occurrences that the speed-amplitude crosses the first threshold over the window meets a second parameter, and
the quantity of occurrences that the speed amplitude crosses the second threshold meets a third parameter.

13. The machine-readable medium of claim 12,
wherein the first parameter comprises a first predetermined range,
wherein the second parameter comprises a second predetermined range,
wherein the third parameter comprises a predetermined value,
wherein determining for the window that the value of the cost function meets the first parameter comprises determining for the window that the value of the cost function is within the first predetermined range;
wherein determining that the quantity of occurrences that the speed-amplitude crosses the first threshold over the window meets the second parameter comprises determining that the quantity of occurrences that the speed-amplitude crosses the first threshold is within the second predetermined range; and
wherein determining that the quantity of occurrences that the speed-amplitude crosses the second threshold meets the third parameter comprises determining that the quantity of occurrences that the speed-amplitude crosses the second threshold exceeds the predetermined value.

14. The machine-readable medium of claim 12, the operations further comprising:
determining for one or more other windows consecutive to the window:
a quantity of occurrences that a speed-amplitude determined for the one or more other windows crosses the first threshold,
a value of the cost function of the speed-amplitude for the one or more other windows, and
a quantity of occurrences that the speed amplitude for the one or more consecutive windows crosses the second threshold; and
wherein identifying the onset of the ventricular fibrillation event comprises determining for the one or more other windows that:
the value of the cost function for the one or more other windows meets the first parameter,
the quantity of occurrences that the speed-amplitude for the one or more other windows crosses the second threshold meets the second parameter, and
the quantity of occurrences that the speed-amplitude for the one or more other windows crosses the third threshold meets the third parameter.

15. The machine-readable medium of claim 9,
wherein the identifying an onset of a ventricular fibrillation event is based on a quantity of occurrences that the speed-amplitude crosses a threshold over the window;
wherein the ECG signal comprises a signal for a first channel and a signal for a second channel;
and the operations further comprising:
determining for the window a maximum of a value of the cost function of the signal for the first channel and a value of the cost function of the signal for second channel, and
determining a maximum value of a quantity of occurrences that the signal for the first channel crosses a predetermined ECG threshold and a quantity of occurrences that the signal for the second channel crosses the predetermined ECG threshold; and
wherein identifying the onset of a ventricular fibrillation event comprises determining the onset of the ventricular fibrillation based on the maximum value of the cost functions for the first channel and the second channel and the maximum value of the quantity of occurrences that the ECG signal crosses the predetermined ECG threshold for the first channel and the second channel.

16. The machine-readable medium of claim 9,
wherein the ECG signal comprises a signal for a first channel and a signal for a second channel; and
wherein determining a speed-amplitude from the analytical pair comprises determining an average of a speed-amplitude for the signal of the first channel and a speed-amplitude for the signal of the second channel.

17. A cardiac monitoring apparatus comprising:
an input element;
a processor; and
a non-transitory machine-readable medium encoding instructions operable to cause the processor to perform operations comprising:
obtaining an ECG signal;
applying a transform to the ECG signal to obtain an analytical pair, the analytical pair including the ECG signal and the transformed ECG signal;
determining a speed-amplitude from the analytical pair; and identifying an onset of a ventricular fibrillation event based on a value of a cost function of the speed-amplitude over a window.

18. The cardiac monitoring apparatus of claim 17, wherein the transformation comprises a Hilbert transformation.

19. The cardiac monitoring apparatus of claim 17,
wherein the identifying an onset of a ventricular fibrillation event is based on a quantity of occurrences that the speed-amplitude crosses a threshold over the window;
wherein the threshold comprises a first threshold; and
wherein identifying the onset of the ventricular fibrillation event comprises identifying the onset of the ventricular fibrillation based on:
the value of the cost function of the speed-amplitude over the window,
the quantity of occurrences that the speed-amplitude crosses the first threshold over the window, and
a quantity of occurrences that the speed amplitude crosses a second, different threshold over the window.

20. The cardiac monitoring apparatus of claim 19, wherein identifying the onset of the ventricular fibrillation event comprises determining for the window that:
the value of the cost function meets a first parameter,
the quantity of occurrences that the speed-amplitude crosses the first threshold over the window meets a second parameter, and
the quantity of occurrences that the speed amplitude crosses the second threshold meets a third parameter.

21. The cardiac monitoring apparatus of claim 20,
wherein the first parameter comprises a first predetermined range,
wherein the second parameter comprises a second predetermined range,
wherein the third parameter comprises a predetermined value,
wherein determining for the window that the value of the cost function meets the first parameter comprises determining for the window that the value of the cost function is within the first predetermined range;
wherein determining that the quantity of occurrences that the speed-amplitude crosses the first threshold over the window meets the second parameter comprises determining that the quantity of occurrences that the speed-amplitude crosses the first threshold is within the second predetermined range; and
wherein determining that the quantity of occurrences that the speed-amplitude crosses the second threshold meets the third parameter comprises determining that the quantity of occurrences that the speed-amplitude crosses the second threshold exceeds the predetermined value.

22. The cardiac monitoring apparatus of claim 20, the operations further comprising:
determining for one or more other windows consecutive to the window:
a quantity of occurrences that a speed-amplitude determined for the one or more other windows crosses the first threshold,
a value of the cost function of the speed-amplitude for the one or more other windows, and
a quantity of occurrences that the speed amplitude for the one or more consecutive windows crosses the second threshold; and
wherein identifying the onset of the ventricular fibrillation event comprises determining for the one or more other windows that:
the value of the cost function for the one or more other windows meets the first parameter,
the quantity of occurrences that the speed-amplitude for the one or more other windows crosses the second threshold meets the second parameter, and
the quantity of occurrences that the speed-amplitude for the one or more other windows crosses the third threshold meets the third parameter.

23. The cardiac monitoring apparatus of claim 17,
wherein the identifying an onset of a ventricular fibrillation event is based on a quantity of occurrences that the speed-amplitude crosses a threshold over the window;
wherein the ECG signal comprises a signal for a first channel and a signal for a second channel;
and the operations further comprising:
determining for the window a maximum of a value of the cost function of the signal for the first channel and a value of the cost function of the signal for second channel, and
determining a maximum value of a quantity of occurrences that the signal for the first channel crosses a predetermined ECG threshold and a quantity of occurrences that the signal for the second channel crosses the predetermined ECG threshold; and
wherein identifying the onset of a ventricular fibrillation event comprises determining the onset of the ventricular fibrillation based on the maximum value of the cost functions for the first channel and the second channel and the maximum value of the quantity of occurrences that the ECG signal crosses the predetermined ECG threshold for the first channel and the second channel.

24. The cardiac monitoring apparatus of claim 17,
wherein the ECG signal comprises a signal for a first channel and a signal for a second channel; and
wherein determining a speed-amplitude from the analytical pair comprises determining an average of a speed-amplitude for the signal of the first channel and a speed-amplitude for the signal of the second channel.

* * * * *